(12) United States Patent
Thomas et al.

(10) Patent No.: US 6,423,837 B1
(45) Date of Patent: Jul. 23, 2002

(54) CLONING AND SEQUENCING OF ALLERGENS OF DERMATOPHAGOIDES HOUSE DUST MITE

(75) Inventors: Wayne Robert Thomas, Nedlands; Kaw-Yan Chua, Nollamara, both of (AU)

(73) Assignee: Immulogic Pharmaceutical Corp., Waltham, MA (US)

( * ) Notice: Subject to any disclaimer, the term of this patent is extended or adjusted under 35 U.S.C. 154(b) by 0 days.

(21) Appl. No.: 09/295,188

(22) Filed: Apr. 20, 1999

Related U.S. Application Data

(63) Continuation-in-part of application No. 08/175,071, filed on Dec. 29, 1993, now abandoned, which is a division of application No. 08/107,332, filed on Aug. 16, 1993, now abandoned, which is a continuation of application No. 07/580,655, filed on Sep. 11, 1990, now abandoned, which is a continuation-in-part of application No. 07/458,642, filed on Feb. 13, 1990, now abandoned.

(51) Int. Cl.[7] .......................... A61K 39/35; A61K 39/36
(52) U.S. Cl. .................... 536/23.5; 536/23.1; 536/23.2; 422/184.1; 422/185.1; 422/275.1; 435/69.3; 435/252.3; 435/252.33; 435/254.2
(58) Field of Search .......................... 424/185.1, 275.1, 424/184.1; 435/69.3, 252.3, 252.33, 254.2, 255.1, 254.11, 320.1, 362; 536/23.2, 23.5, 23.1

(56) References Cited

U.S. PATENT DOCUMENTS

| | | | | |
|---|---|---|---|---|
| 5,798,099 A | * | 8/1998 | Yuuki et al. | 424/185.1 |
| 5,876,722 A | * | 3/1999 | Yuuki et al. | 424/185.1 |

FOREIGN PATENT DOCUMENTS

| | | |
|---|---|---|
| AU | 3132771 | 1/1973 |
| WO | WO 88/10297 | 12/1988 |

OTHER PUBLICATIONS

Chapman et al. (1987) "Epitope Mapping of Major Dust Mite (dermatophagoides) Allergens Using Monoclonal Antibodies" *Mite Allergy* :27–29.
Chua et al. (1990) "Expression of Dermatophagoides Pteronyssinus Allergen, Der p II, in Escherichia Coli and the Binding Studies with Human IgF" *Chemical Abstracts* 113: 434 (Abstract No. 4264).
Chua et al. (1990) "Isolation of cDNA Coding for the Major Mite Allergen Der p II by IgE Plaque Immunoassay" *Int. Arch. Allergy Appl. Immun.* 91: 118–123.
Chua et al. "Sequence Analysis to cDNA Coding for a major Proteases" *Chemical Abstracts* 108(217095): 148.
Ford et al. (1989) "The Spectrum of Low Molecular Weight House Dust Mite (Dermatophagoides Pteronyssinus) Allergens with Emphasis on Der p II" *Clinical and Experimental Allergy* 20: 27–31.
Greene et al. (1990) "Antigenic Analysis of Group I House Dust Mite Allergens Using Random Fragments of Der p I Expresed by Recombant DNA Libraries" *Int. Arch. Allergy Appl. Immun.* 92: 30–38.
Griffin et al. (1989) "Allergenic and Antigenic Relationship Between Three Species of Storage Mite and the House Dust Mite, Dermatophagoides Pteronyssinus" *J. Allergy Clin. Immun.* 84:108–117.
Heyman et al. (1986) "Antigen Der f I from the Dust Mite Dermatophagoides Farinae: Structural Comparison with Der p I from Dermatophagoides Pteronyssinus and Epitope Specificity of Murine IgG and Human IgE Antibodies" *Journal of Immunology* 137: 2841–2847.
Heyman et al. (1989) "Antigenic and Structural Analysis of Group II Allergens (Der f II and Der p II) from House Dust Mites (Dermatophagoides spp)" *J. Allergy Clin. Immun.* 83: 1055–1067.
Krilis et al. (1984) "Antigens and Allergens from the Common House Dust Mite Dermatophagoides Pteronyssinus" *J Allergy & Clin Immun.* 74: 142–6.
Lamb et al. (1989) "HLA Class II Restriction Specificity of Dermatophagoides spp. Reactive T Lymphocyte Clones that Support IgE Syntesis" *Clinical and Exper. Allergy* 19: 389–393.
Lamb et al. (1988) "The Use of Nitrocellulose Immunoblots for the Analysis of Antigen Recognition by T Lymphocytes" *Journal of Immunological Methods* 110: 1–10.
O'Hehir et al. (1986) "Colonal Analysis of the Cellular Immune Response to the House Dust Mite Cematophagoides Farinae" *Int. Arch. Allergy Appl. Immun.* 88: 170–172.
Pierce et al. (1986) "Molecular Cloning of *Schistosama masoni* Allergens" *Biochemical Genetics* 109: 191 (Abstract No. 143703).
Stewart (1982) "Isolation and Characterization of the Allergen Dpt 12 from *Dermatophagoides pteronyssinus* by Chromatofocusing" *Int. Arch. Allergy Appl. Immun.* 69: 224–230.
Stewart and Holt (1987) "Immunogenicity and Tolerogenicity of a Major House Dust Mite Allergen, der p I from *Dermatophasgoides pteronyssinus*, in Mice and Rats" *Int. Archs. Allergy Appl. Immun.* 83(1): 44–51.

(List continued on next page.)

Primary Examiner—Laurie Scheiner
(74) *Attorney, Agent, or Firm*—Lahive & Cockfield, LLP; Jane E. Remillard, Esq.; Jeanne M. DiGiorgio, Esq.

(57) ABSTRACT

Isolated DNA encoding allergens of Dermatophagoides (house dust mites) particularly of the species *Dermatophagoides farinae* and *Dermatophagoides pteronyssinus*, which are protein allergens or peptides which include at least one epitope of the protein allergen. In particular, DNA encoding two major *D. farinae* allergens, *Der f* I and *Der f* II and DNA encoding a *D. pteronyssinus* allergen, *Der p* I. In addition, the proteins or peptides encoded by the isolated DNA, their use as diagnostic and therapeutic reagents and methods of diagnosing and treating sensitivity to house dust mite allergens.

11 Claims, 12 Drawing Sheets

OTHER PUBLICATIONS

Stewart et al. (1988) "An Allergen & Antigenic Mapping Analysis of a Major Mite Allergen, Der p I" Proceedings of the DPC 1st International Symposium on Allergy & Molecular Biology, *Advances in Biosciences: Allergy and Molecular Biology* 74: 297–310.

Stewart et al. (1989) "Epitope Mapping Analysis of the Major Mite Allergens Using Synthetic Peptides" *Proceedings of the Workshop of the XIV Congress of the European Academy of Allergy and Clinical Immunology*, Berlin.

Stewart et al. (1987) "In vitro Translation of Messenger RNA from House Dust Mite Dermatophagoides Pteronyssinus" *Int. Archs. Allergy Appl. Immun.* 83: 384–359.

Stewart et al. (1986) "The Physiochemical Characterization of a Major Protein Allergen from the House Dust Mite, *Dermatophagoides pteronyssinus*" *Asian Pacific J. of Allergy & Immun.* 4(1):71.

Thomas et al. (1990) "Analysis and Expression of cDNA Clones Coding for House Dust Mite Allergens" *Biochem. Genetics* 113: 179 (Abstract No. 72092f).

Thomas et al. (1988) "Cloning and Expression of DNA Coding for the Major House Dust Mite Allergen Der p I in *Escherichia coli*" *Int. Archs. Appl. Immun.* 85: 127–129.

Thomas et al. (1987) "Expression of the House Dust Mite Allergen Der p I in E. Coli" The UCB Institute of Allergy, *Mite Allergy* 34–40.

Thomas et al. (1989) "Recombinant Mite Allergens" *Proceedings of the Workshop of the XIV Congress of the European Academy of Allergy an Clinical Immunology*, Berlin.

Tovey et al. (1989) "Cloning and Sequencing of cDNA Expressing a Recombinant House Dust Mite Protein that Binds Human IgE and Corresponds to an Important Low Molecular Weight Allergen" *J. Exp. Med.* 170: 1457–1462.

Yasueda et al. (1986) "Isolation and Characterization of Two Allergens from *Dermatophagoides farinae*" *Int. Archs. Allergy Appl. Immun.* 105: 552 (Abstract No. 189004e).

Young et al. (1983) "Efficient Isolation of Genes Using Antibody Probes" *Proc. Natl. Acad. Sci. USA* 80: 1194–1198.

Yuuki et al. (1990) "Cloning and Sequencing of cDNAs Corresponding to Mite Major Allergen der f II" *Japanese Journal of Allergology* 39(6): 557–561.

* cited by examiner

```
                                                           -98
       GAATTCCGTTTTCTTCCATCAAAATTAAAAATTCATCAAAA ATG AAA TTC GTT TTG GCC ATT    62
                                                Met Lys Phe Val Leu Ala Ile
          -90                                           ↓-80
GCC TCT TTG TTG GTA TTG AGC ACT GTT TAT GCT CGT CCA GCT TCA ATC AAA ACT    116
Ala Ser Leu Leu Val Leu Ser Thr Val Tyr Ala Arg Pro Ala Ser Ile Lys Thr
            -70                                         -60
TTT GAA GAA TTC AAA AAA GCC TTC AAC AAA AAC TAT GCC ACC GTT GAA GAG GAA    170
Phe Glu Glu Phe Lys Lys Ala Phe Asn Lys Asn Tyr Ala Thr Val Glu Glu Glu
                    -50                                         -40
GAA GTT GCC CGT AAA AAC TTT TTG GAA TCA TTG AAA TAT GTT GAA GCT AAC AAA    224
Glu Val Ala Arg Lys Asn Phe Leu Glu Ser Leu Lys Tyr Val Glu Ala Asn Lys
                            -30                                         -20
GGT GCC ATC AAC CAT TTG TCC GAT TTG TCA TTG GAT GAA TTC AAA AAC CGT TAT    278
Gly Ala Ile Asn His Leu Ser Asp Leu Ser Leu Asp Glu Phe Lys Asn Arg Tyr
                                    -10
TTG ATG AGT GCT GAA GCT TTT GAA CAA CTC AAA ACT CAA TTC GAT TTG AAT GCC    332
Leu Met Ser Ala Glu Ala Phe Glu Gln Leu Lys Thr Gln Phe Asp Leu Asn Ala
-1 ↓ 1                                    10
GAA ACA AGC GCT TGC CGT ATC AAT TCG GTT AAC GTT CCA TCG GAA TTG GAT TTA    386
Glu Thr Ser Ala Cys Arg Ile Asn Ser Val Asn Val Pro Ser Glu Leu Asp Leu
        20                                          30
CGA TCA CTG CGA ACT GTC ACT CCA ATC CGT ATG CAA GGA GGC TGT GGT TCA TGT    440
Arg Ser Leu Arg Thr Val Thr Pro Ile Arg Met Gln Gly Gly Cys Gly Ser Cys
                40                                          50
TGG GCT TTC TCT GGT GTT GCC GCA ACT GAA TCA GCT TAT TTG GCC TAC CGT AAC    494
Trp Ala Phe Ser Gly Val Ala Ala Thr Glu Ser Ala Tyr Leu Ala Tyr Arg Asn
                        60                                          70
ACG TCT TTG GAT CTT TCT GAA CAG GAA CTC GTC GAT TGC GCA TCT CAA CAC GGA    548
Thr Ser Leu Asp Leu Ser Glu Gln Glu Leu Val Asp Cys Ala Ser Gln His Gly
                                80
TGT CAC GGC GAT ACA ATA CCA AGA GGC ATC GAA TAC ATC CAA CAA AAT GGT GTC    602
Cys His Gly Asp Thr Ile Pro Arg Gly Ile Glu Tyr Ile Gln Gln Asn Gly Val
 90                                          100
GTT GAA GAA AGA AGC TAT CCA TAC GTT GCA CGA GAA CAA CGA TGC CGA CGA CCA    656
Val Glu Glu Arg Ser Tyr Pro Tyr Val Ala Arg Glu Gln Arg Cys Arg Arg Pro
            110                                         120
AAT TCG CAA CAT TAC GGT ATC TCA AAC TAC TGC CAA ATT TAT CCA CCA GAT GTG    710
Asn Ser Gln His Tyr Gly Ile Ser Asn Tyr Cys Gln Ile Tyr Pro Pro Asp Val
                    130                                         140
AAA CAA ATC CGT GAA GCT TTG ACT CAA ACA CAC ACA GCT ATT GCC GTC ATT ATT    764
Lys Gln Ile Arg Glu Ala Leu Thr Gln Thr His Thr Ala Ile Ala Val Ile Ile
                            150                                         160
GGC ATC AAA GAT TTG AGA GCT TTC CAA CAT TAT GAT GGA CGA ACA ATC ATT CAA    818
Gly Ile Lys Asp Leu Arg Ala Phe Gln His Tyr Asp Gly Arg Thr Ile Ile Gln
```

Fig. 2A

```
                                     170
CAT GAC AAT GGT TAT CAA CCA AAC TAT CAT GCC GTC AAC ATT GTC GGT TAC GGA   872
His Asp Asn Gly Tyr Gln Pro Asn Tyr His Ala Val Asn Ile Val Gly Tyr Gly
180                                              190
AGT ACA CAA GGC GAC GAT TAT TGG ATC GTA CGA AAC AGT TGG GAT ACT ACC TGG   926
Ser Thr Gln Gly Asp Asp Tyr Trp Ile Val Arg Asn Ser Trp Asp Thr Thr Trp
            200                                              210
GGA GAT AGC GGA TAC GGA TAT TTC CAA GCC GGA AAC AAC CTC ATG ATG ATC GAA   980
Gly Asp Ser Gly Tyr Gly Tyr Phe Gln Ala Gly Asn Asn Leu Met Met Ile Glu
                    220         223
CAA TAT CCA TAT GTT GTA ATC ATG TGAACATTTGAAATTGAATATATTTATTTGTTTTCAAAAT 1044
Gln Tyr Pro Tyr Val Val Ile Met
AAAAACAACTACTCTTGCGAGTATTTTTTACTCGGAATTC 1084
```

Fig. 2B

```
              10        20        30        40        50        60
Der p 1   TNACSING*NAPAEIDLRQMRTVTPIRMQGGCGSCWAFSGVAATESAYLAHRNQSLDLAEQE
Der f 1   .S..R..SV.V.S.L...SL........................Y..T....S...

70        80        90       100       110       120
Der p 1   LVDCASQHGCHGDTIPRGIEYIQHNGVVQESYYRYVAREQSCRRPNAQRFGISNYCQIYPPN
Der f 1   ......................Q....E.RS.P......R.....S.HY...........D 130       140       150       160       170       180
Der p 1   ANKIREALAQTHSAIAVIIGIKDLDAFRHYDGRTIIQRDNGYQPNYHAVNIVGYSNAQGVDY
Der f 1   VKQ.....T...T...........R..Q.........H.............GST..D..

190       200       210       220
Der p 1   WIVRNSWDTNWGDNGYGYFAANIDLMMIEEYPYVVIL
Der f 1   ........T...S.....Q.GNN.....Q......M
```

Fig. 3

```
Cathepsin H    MWTALPLLCAGAWLLSAGATA------------------ELTY-NA-IEKFH---FTSWMKQHOKTY-SS-
Cathepsin L     MTPLLLAVLCLGTALA----------------TPKFDQ-TF-NAQWH-----QWKSTHRRLY-GT-
Papain         MAMIPSISKLLFVAICLFVYMGLSFG----------DFSIVGYSQNDLTS-TE-RLIQL--FESWMLKHNKIYKNI-
Aleurain       MAHARVLLALAVLATAAVAYASSSSFADSNPIRPVTDRAASTLESAVLGALGRTHAALRFARFAVRYGKSYESA-
CP1                MKVILLFVLAVFTVF-----------VSSRGIPPEEQ-SQ-FLEFQ---DKFNKKYSHEEY-LE-
CP2                MRLLVFLILIFVNFSFA-----------NVRPNGRRFS-ES-QYRTA---FTEWTLKFNRQY-SS-
Cathepsin B        MWWSLIPLSCLLALTSA---------------------------------HDK---PS-
CTLA-2α        MVSICEQKLQHFSAVFLLILCLGMMSA---------------------APPPDPSLDNEWKEWKTKFAKAYNLN-
CTLA-2β        MVSICEQKLQHFSAVFLLILCLGMMSA---------------------APSPDPSLDNEWKEWKTTFAKAYSLD-
MCP              NLLLAVLCLGTALA---------------------TPKFDQTFSAEWHQWKSTHRRLY-GT-
Der f I        MKFVLAIASLLVLSTVYA---------------------RPASIKTFEEFKKAFNKNYATVE
                                                       *  *        *   *   *
```

```
Cathepsin H    REYSHRLQVFANNWRKIQAHN--QRN--HTFKMG--LNQFSDMSFAEIKIKYL-WSE-PQNCS--AT-KS--NYL--RGTGP
Cathepsin L    NEEEWRRAVWEKNMRMIQIHNGEYSNGKHGFIHE--MNAFGDMTNEEFRQIVN-GYR-HQKHK--KG-RL--FQE--PLMLQ
Papain         DEKIYRFEIFKDNLKYIDETN--KKN--NSYWLG--LNVFADMSNDEFKEKYT-GSI-AGNYT--TTELSYEEVL-NDGDVN
Aleurain       AEVRRRFRIFSESLEEVRSTN--RKG--LPYRLG--INRFSDMSWEEFQATRL-GA--AQTCS--ATLAG--NHL-MRDAAA
CP1            RFEIFKSNLGKIEELNLIAIN--HKA--DT-KFG--VNKFADLSSDEFKNYYLNNKEAIFTDD--LP-VA--DYLDDEFINS
CP2            SEFSNRYSIFKSNMDYVDNWN--SKGD--SQTVLG--LNNFADITNEEYRKTYL-GTR-VNAHSYNGYDGR-;EVLNVEDLQT
Cathepsin B    ---FHPLS---DDM--INYIN--KQN--TTWQAG--RN-EYNV-DISYLKKPC-GTV-LGGPK--LP-ER--VGF--SEDIN
CTLA-2α        NEEERHRRLVWEENKKKIEAHNADYEQGKTSFYMG--LNQFSDLTPEEFKTNCY-GNSLNRGEM
CTLA-2β        DEERHRRLMWEENKKKIEAHNADYERGKTSFYMG--LNQFSDLTPEEFRTNCC-GSSMCRGEM
MCP            NEEEWRRAIWEKNMRMIQLHNGEYSNGQHGFSME--MNAFGDMTNEEFRQVVN-GYRHQKHKK
Der p I                       --KNRFL-MS-AEAFEH-L-KTQFRLNAE
Actinidin                 LRFIDEHNAD--TNR--SYKVG--LNQFADLTGEEFRSTYL-G
Der f I        EEEVARKN-FLESLKYVEA-NKGAINHLSDLSLDEFKNRYL-MS-AEAFEQ-L-KTQFDLNAE
               * *        *         *          *     *   **.. **     *
                                                                *     *
```

Fig. 4

```
                                              10
GAT CAA GTC GAT GTT AAA GAT TGT GCC AAC AAT GAA ATC AAA AAA GTA ATG    51
Asp Gln Val Asp Val Lys Asp Cys Ala Asn Asn Glu Ile Lys Lys Val Met 20                                     30
GTC GAT GGT TGC CAT GGT TCT GAT CCA TGC ATC ATC CAT CGT GGT AAA CCA   102
Val Asp Gly Cys His Gly Ser Asp Pro Cys Ile Ile His Arg Gly Lys Pro 40                                      50
TTC ACT TTG GAA GCC TTA TTC GAT GCC AAC CAA AAC ACT AAA ACC GCT AAA   153
Phe Thr Leu Glu Ala Leu Phe Asp Ala Asn Gln Asn Thr Lys Thr Ala Lys

60
ACT GAA ATC AAA GCC AGC CTC GAT GGT CTT GAA ATT GAT GTT CCC GGT ATT   204
Thr Glu Ile Lys Ala Ser Leu Asp Gly Leu Glu Ile Asp Val Pro Gly Ile 70                                     80
GAT ACC AAT GCT TGC CAT TTT ATG AAA TGT CCA TTG GTT AAA GGT CAA CAA   255
Asp Thr Asn Ala Cys His Phe Met Lys Cys Pro Leu Val Lys Gly Gln Gln 90                                     100
TAT GAT GCC AAA TAT ACA TGG AAT GTG CCG AAA ATT GCA CCA AAA TCT GAA   306
Tyr Asp Ala Lys Tyr Thr Trp Asn Val Pro Lys Ile Ala Pro Lys Ser Glu

110
AAC GTT GTC GTT ACA GTC AAA CTT GTT GGT GAT AAT GGT GTT TTG GCT TGC   357
Asn Val Val Val Thr Val Lys Leu Val Gly Asp Asn Gly Val Leu Ala Cys 120                                     129
GCT ATT GCT ACC CAC GCT AAA ATC CGT GAT TAAAAAAAAAAAAATAAATATGAAAATT   414
Ala Ile Ala Thr His Ala Lys Ile Arg Asp

TTCACCAACATCGAACAAAATTCAATAACCAAAATTTGAATCAAAAACGGAATTCCAAGCTGAGCGC   481

CGGTCGCTAC                                                            491
```

Fig. 6

```
     -23                                                      -10
     AAA AAC CGA TTT TTG ATG AGT GCA GAA GCT TTT GAA CAC CTC AAA ACT   48
     Lys Asn Arg Phe Leu Met Ser Ala Glu Ala Phe Glu His Leu Lys Thr
                                 -1  1
     CAA TTC GAT TTG AAT GCT GAA ACT AAC GCC TGC AGT ATC AAT GGA AAT   96
     Gln Phe Asp Leu Asn Ala Glu Thr Asn Ala Cys Ser Ile Asn Gly Asn
      10                                      20
     GCT CCA GCT GAA ATC GAT TTG CGA CAA ATG CGA ACT GTC ACT CCC ATT  144
     Ala Pro Ala Glu Ile Asp Leu Arg Gln Met Arg Thr Val Thr Pro Ile
                     30                                          40
     CGT ATG CAA GGA GGC TGT GGT TCA TGT TGG GCT TTC TCT GGT GTT GCC  192
     Arg Met Gln Gly Gly Cys Gly Ser Cys Trp Ala Phe Ser Gly Val Ala
                                         50
     GCA ACT GAA TCA GCT TAT TTG GCT CAC CGT AAT CAA TCA TTG GAT CTT  240
     Ala Thr Glu Ser Ala Tyr Leu Ala His Arg Asn Gln Ser Leu Asp Leu
                 60                                      70
     GCT GAA CAA GAA TTA GTC GAT TGT GCT TCC CAA CAC GGT TGT CAT GGT  288
     Ala Glu Gln Glu Leu Val Asp Cys Ala Ser Gln His Gly Cys His Gly
                                     80
     GAT ACC ATT CCA CGT GGT ATT GAA TAC ATC CAA CAT AAT GGT GTC GTC  336
     Asp Thr Ile Pro Arg Gly Ile Glu Tyr Ile Gln His Asn Gly Val Val
      90                                     100
     CAA GAA AGC TAC TAT CGA TAC GTT GCA CGA GAA CAA TCA TGC CGA CGA  384
     Gln Glu Ser Tyr Tyr Arg Tyr Val Ala Arg Glu Gln Ser Cys Arg Arg
                     110                                        120
     CCA AAT GCA CAA CGT TTC GGT ATC TCA AAC TAT TGC CAA ATT TAC CCA  432
     Pro Asn Ala Gln Arg Phe Gly Ile Ser Asn Tyr Cys Gln Ile Tyr Pro
                                     130
     CCA AAT GCA AAC AAA ATT CGT GAA GCT TTG GCT CAA ACC CAC AGC GCT  480
     Pro Asn Ala Asn Lys Ile Arg Glu Ala Leu Ala Gln Thr His Ser Ala
                 140                                     150
     ATT GCC GTC ATT ATT GGC ATC AAA GAT TTA GAC GCA TTC CGT CAT TAT  528
     Ile Ala Val Ile Ile Gly Ile Lys Asp Leu Asp Ala Phe Arg His Tyr
                                 160
     GAT GGC CGA ACA ATC ATT CAA CGC GAT AAT GGT TAC CAA CCA AAC TAT  576
     Asp Gly Arg Thr Ile Ile Gln Arg Asp Asn Gly Tyr Gln Pro Asn Tyr
     170                                     180
     CAC GCT GTC AAC ATT GTT GGT TAC AGT AAC GCA CAA GGT GTC GAT TAT  624
     His Ala Val Asn Ile Val Gly Tyr Ser Asn Ala Gln Gly Val Asp Tyr
                         190                                     200
     TGG ATC GTA CGA AAC AGT TGG GAT ACC AAT TGG GGT GAT AAT GGT TAC  672
     Trp Ile Val Arg Asn Ser Trp Asp Thr Asn Trp Gly Asp Asn Gly Tyr
                                         210
     GGT TAT TTT GCT GCC AAC ATC GAT TTG ATG ATG ATT GAA GAA TAT CCA  720
     Gly Tyr Phe Ala Ala Asn Ile Asp Leu Met Met Ile Glu Glu Tyr Pro
                 220     222
     TAT GTT GTC ATT CTC TAAACAAAAGACAATTTCTTATATGATTGTCACTAATTTATT  778
     Tyr Val Val Ile Leu
     TAAATCAAAATTTTTAGAAAATGAATAAATTCATTCACAAAAATTAAAAAAAAAAAAAAAAAA  841
     AAAAAAAAAAAAAAAA   857
```

Fig. 7

```
Dp II: CACAAATTCTTCTTTCTTCCTTACTACTGATCATTAATCTGAAAACAAAACCAAACAAACCAT   63

-16                      -10
Dp II: TCAAAATGATG TAC AAA ATT TTG TGT CTT TCA TTG TTG GTC GCA GCC GTT   113
                  Tyr Lys Ile Leu Cys Leu Ser Leu Leu Val Ala Ala Val
              Met

-1   1                                10
Dp II: GCT CGT GAT CAA GTC GAT GTC AAA GAT TGT GCC AAT CAT GAA ATC AAA   161
       Ala Arg Asp Gln Val Asp Val Lys Asp Cys Ala Asn His Glu Ile Lys

Df II:         ... ... ... ... ..T ... ... ... ... ..C A.. ... ... ...    42
                                                       Asn 20                                      30
Dp II: AAA GTT TTG GTA CCA GGA TGC CAT GGT TCA GAA CCA TGT ATC ATT CAT   209
       Lys Val Leu Val Pro Gly Cys His Gly Ser Glu Pro Cys Ile Ile His

Df II: ... ..A A.. ..C GAT ..T ... ... ... ..T ..T ... ..C ... ..C ...    90
               Met     Asp                   Asp

40
Dp II: CGT GGT AAA CCA TTC CAA TTG GAA GCC GTT TTC GAA GCC AAC CAA AAC   257
       Arg Gly Lys Pro Phe Gln Leu Glu Ala Val Phe Glu Ala Asn Gln Asn

Df II: ... ... ... ... ... ACT ... ... ... T.A ... ..T ... ... ... ...   138
                           Thr               Leu     Asp 50                                          60
Dp II: ACA AAA ACG GCT AAA ATT GAA ATC AAA GCC TCA ATC GAT GGT TTA GAA   305
       Thr Lys Thr Ala Lys Ile Glu Ile Lys Ala Ser Ile Asp Gly Leu Glu

Df II: ..T ... ..C ... ... .C. ... ... ... ... AGC C.. ... ... C.T ...   186
                                               Thr                Leu

70
Dp II: GTT GAT GTT CCC GGT ATC GAT CCA AAT GCA TGC CAT TAC ATG AAA TGC   353
       Val Asp Val Pro Gly Ile Asp Pro Asn Ala Cys His Tyr Met Lys Cys

Df II: A.. ... ... ... ... ..T ... A.C ... ..T ... ... .TT ... ... ..T   234
       Ile                         Thr                 Phe
```

Fig. 9A

```
       80                                                90
Dp II: CCA TTG GTT AAA GGA CAA CAA TAT GAT ATT AAA TAT ACA TGG AAT GTT  401
       Pro Leu Val Lys Gly Gln Gln Tyr Asp Ile Lys Tyr Thr Trp Asn Val

Df II: ... ... ... ... ..T ... ... ... ... GCC ... ... ... ... ... ..G  282
                                           Ala 100                                      110
Dp II: CCG AAA ATT GCA CCA AAA TCT GAA AAT GTT GTC GTC ACT GTT AAA GTT  449
       Pro Lys Ile Ala Pro Lys Ser Glu Asn Val Val Val Thr Val Lys Val

Df II: ... ... ... ... ... ... ... ..C ... ... ..T ..A ..C ... C..      330
                                                                 Leu

120
Dp II: ATG GGT GAT GAT GGT GTT TTG GCC TGT GCT ATT GCT ACT CAT GCT AAA  497
       Met Gly Asp Asp Gly Val Leu Ala Cys Ala Ile Ala Thr His Ala Lys

Df II: G.T ... ... A.. ... ... ... ..T ..C ... ... ... ..C ..C ... ...  378
       Val         Asn

129
Dp II: ATC CGC GAT TAA ATCAAACAAAATTTATTGATTTTGTAATCACAAATGATTGATTTTCTT 557
       Ile Arg Asp END

Df II: ... ..T ... ... .AA...A...TAAATA...AAA.T.TCA.CA.C..CGAAC.AAA.TCA 438

Dp II: TCCAAAAAAAAAATAAATAAAATTTTGGGAATTC                                591

Df II: ATA.CC....TTTG..TC....AC___GGAATTC                                469
```

Fig. 9B

CLONING AND SEQUENCING OF ALLERGENS OF DERMATOPHAGOIDES HOUSE DUST MITE

RELATED APPLICATION

This application is a continuation of application Ser. No. 08/175,071, filed Dec. 29, 1993, now abandoned, which is a divisional of application Ser. No. 08/107,332, filed Aug. 16, 1993, now abandoned which is a continuation of application Ser. No. 07/580,655, filed on Sep. 11, 1990, now abandoned, which is a Continuation-In-Part of U.S. Ser. No. 458,642 entitled "Cloning of Mite Allergens", by Wayne Robert Thomas, Geoffrey Alexander, Stewart Keven James Turner and Richard John Simpson (filed Feb. 13, 1990), now abandoned. The teachings of application U.S. Ser. No. 458,642 are incorporated herein by reference.

FUNDING

Work described herein was funded by grants from the Princess Margaret Children's Medical Research Foundation, the Australian Health and Medical Research Council and the Asthma Foundation of Australia.

BACKGROUND

Recent reports have documented the importance of responses to the Group I and Group II allergens in house dust mite allergy. For example, it has been documented that over 60% of patients have at least 50% of their anti-mite antibodies directed towards these proteins (Lind, P. et al., *Allergy*, 39:259–274 (1984); van der Zee, J. S. et al., *J. Allergy Clin. Immunol.*, 81:884–896 (1988)). It is possible that children show a greater degree of reactivity (Thompson, P. J. et al, *Immunology*, 64:311–314 (1988)). Allergy to mites of the genus Dermatophagoides (D.) is associated with conditions such as asthma, rhinitis and ectopic dermatitis. Two species, *D. pteronyssinus* and *D. farinae*, predominate and, as a result, considerable effort has been expended in trying to identify the allergens produced by these two species. *D. pteronyssinus* mites are the most common Dermatophagoides species in house dust in Western Europe and Australia. The species *D. farinae* predominates in other countries, such as, North America and Japan (Wharton, G. W., *J. Medical Entom*, 12:577–621 (1976)). It has long been recognized that allergy to mites of this genus is associated with diseases such as asthma, rhinitis and atopic dermatitis. It is still not clear what allergens produced by these mites are responsible for the allergic response and associated conditions.

SUMMARY OF THE INVENTION

The present invention relates to isolated DNA which encodes a protein allergen of Dermatophagoides (D.) house dust mite) or a peptide which includes at least one epitope of a protein allergen of a house dust mite of the genus Dermatophagoides. It particularly relates to DNA encoding major allergens of the species *D. farinae*, designated *Der f* I and *Der f* II, or portions of these major allergens (i.e., peptides which include at least one epitope of *Der f* I or of *Der f* II). It also particularly relates to DNA encoding major allergens of *D. pteronyssinus*, designated *Der p* I and *Der p* II, or portions of these major allergens (i.e., peptides which include at least one epitope of *Der p* I or of *Der p* II).

The present invention further relates to proteins and peptides encoded by the isolated Dermatophagoides (e.g., *D. farinae, D. pteronyssinus*) DNA. Peptides of the present invention include at least one epitope of a *D. farinae* allergen (e.g., at least one epitope of *Der f* I or of *Der f* II) or at least one epitope of a *D. pteronyssinus* allergen (e.g., at least one epitope of *Der p* I or of *Der p* II). It also relates to antibodies specific for *D. farinae* proteins or peptides and to antibodies specific for *D. pteronyssinus* proteins or peptides.

Dermatophagoides DNA, proteins and peptides of the present invention are useful for diagnostic and therapeutic purposes. For example, isolated *D. farinae* protein or peptide can be used to detect sensitivity in an individual to house dust mites and can be used to treat sensitivity (reduce sensitivity or desensitize) in an individual, to whom therapeutically effective quantities of the *D farinae* protein or peptide is administered. For example, isolated *D. farinae* protein allergen, such as *Der f* I or *Der f* II can be administered periodically, using standard techniques, to an individual in order to desensitize the individual. Alternatively, a peptide which includes at least one epitope of *Der f* I or of *Der f* II can be administered for this purpose. Isolated *D. pteronyssinus* protein allergen, such as *Der p* I or *Der p* II, can be administered as described for *Der f* I or *Der f* II. Similarly a peptide which includes at least one *Der p* I epitope or at least one *Der p* II epitope can be administered for this purpose. A combination of these proteins or peptides (e.g., *Der f* I and *Der f* II; *Der p* I and *Der p* II; or a mixture of both *Der f* and *Der p* proteins) can also be administered. The use of such isolated proteins or peptides provides a means of desensitizing individuals to important house dust mite allergens.

BRIEF DESCRIPTION OF THE DRAWINGS

FIG. 2 is the nucleotide sequence and the predicted amino acid sequence of cDNA λgt11 f 1. Numbers above are nucleotide positions; numbers to the left are amino acid positions. Positive amino acid residue numbers correspond to the sequence of the mature excreted *Der f* I beginning with threonine. Negative sequence numbers refer to the signal peptide and the proenzyme regions of *Der f* I. The arrows indicate the beginning of the proenzyme sequence and the mature *Der f* I, respectively. The underlined residues −81 to −78 make up the proposed cleavage site for the proenzyme formation, while the underlined residues 53–55 represent a potential N-glycosylation site. The termination TGA codon and the adjacent polyadenylation signal are also underlined. Amino acid residues 1–28 correspond to a known tryptic peptide sequence determined by conventional amino acid sequencing analysis.

FIG. 3 is a composite alignment of the amino acid sequences of the mature *Der p* I and *Der f* I proteins. The numbering above the sequence refers to *Der p* I. The asterisk denotes the gap that was introduced for maximal alignment. The symbol (.) is used to indicate that the amino acid residue of *Der f* I at that position is identical to the corresponding amino acid residue of *Der p* I. The arrows indicate those residues making up the active site of *Der p* I and *Der f* I.

FIG. 4 is a comparison of the amino acid sequence the pre- and pro-peptide regions of *Der f* I with those of rat cathepsin H, rat cathepsin L, papain, aleurain, CP1, CP2, rat cathepsin B, CTLA-2, MCP, *Der p* I and actinidin. Gaps, denoted by dashes, were added for maximal alignment. Double asterisks denote conserved amino acid residues which are shared by greater than 80% of the proenzymes;

single asterisks show residues which are conserved in greater than 55% of the sequences. The symbol (.) is used to denote semiconserved equivalent amino acids which are shared by greater than 90% of the proenzyme regions.

Figure 5:
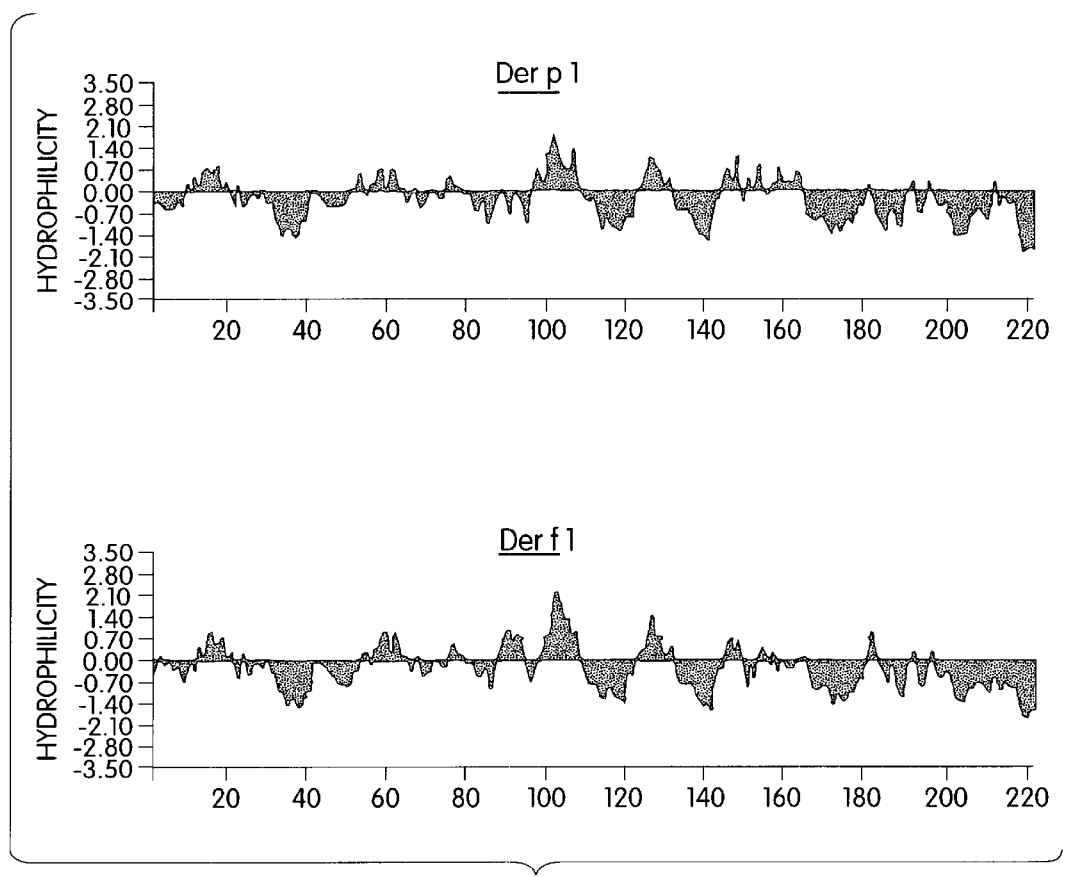

FIG. 5 is a hydrophilicity plot of the *Der p* I mature protein and a hydrophilicity plot of the *Der f* I mature protein produced using the Hopp-Woods algorithm computed with the Mac Vector Sequence Analysis Software (IBI, New Haven) using a 6 residue window. Positive values indicate relative hydrophilicity and negative values indicating relative hydrophobicity.

FIG. 6 is the nucleotide sequence and the predicted amino acid sequence of *Der f* II cDNA. Numbers to the right are nucleotide positions and numbers above are amino acid residues. The stop (TAA) signal is underlined. The first 8 nucleotides are from the oligonucleotide primer used to generate the cDNA, based on the *Der p* II sequence.

FIG. 7 is the nucleotide sequence and predicted amino acid sequence of cDNA λgt11 p1(13T). Numbers to the right are nucleotides and numbers above are amino acid positions. Positive amino acids correspond to the sequence of mature excreted *Der p* I beginning with threonine.

Figure 8:
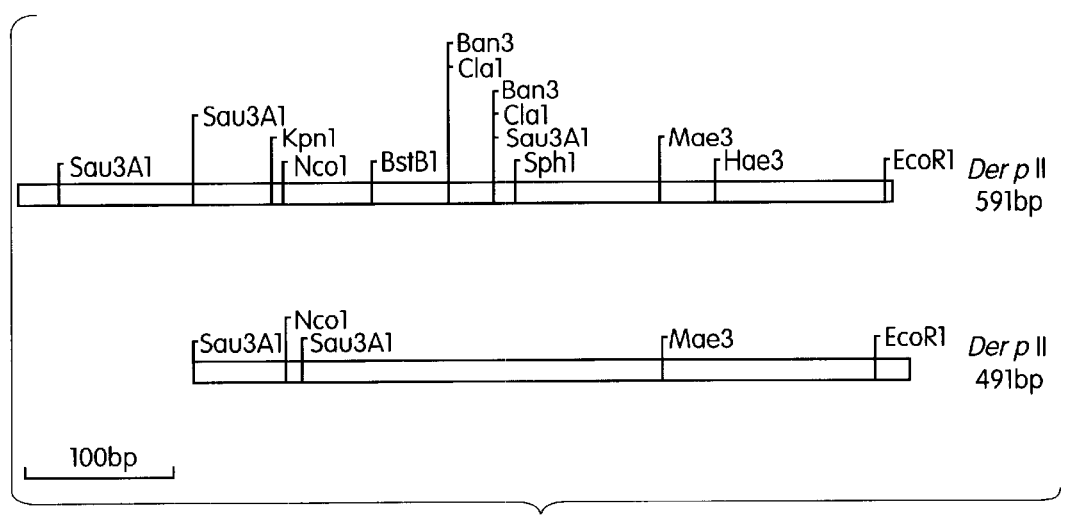

FIG. 8 is a restriction map of *Der f* II cDNA, which was generated by computer from the sequence data. A map of *Der p* II similarly generated is shown for comparison. There are few common restriction enzyme sites conserved. Sites marked with an asterisk were introduced by cloning procedures.

FIG. 9 hows the alignment of *Der f* II and *Der p* II cDNA sequences. Numbers to the right are nucleotide position and numbers above and amino acid residues. The top line gives the *Der p* II nucleotide sequence and the second the *Der p* II amino acid residues. The next two lines show differences of *Der f* II to these sequences.

Figure 10:
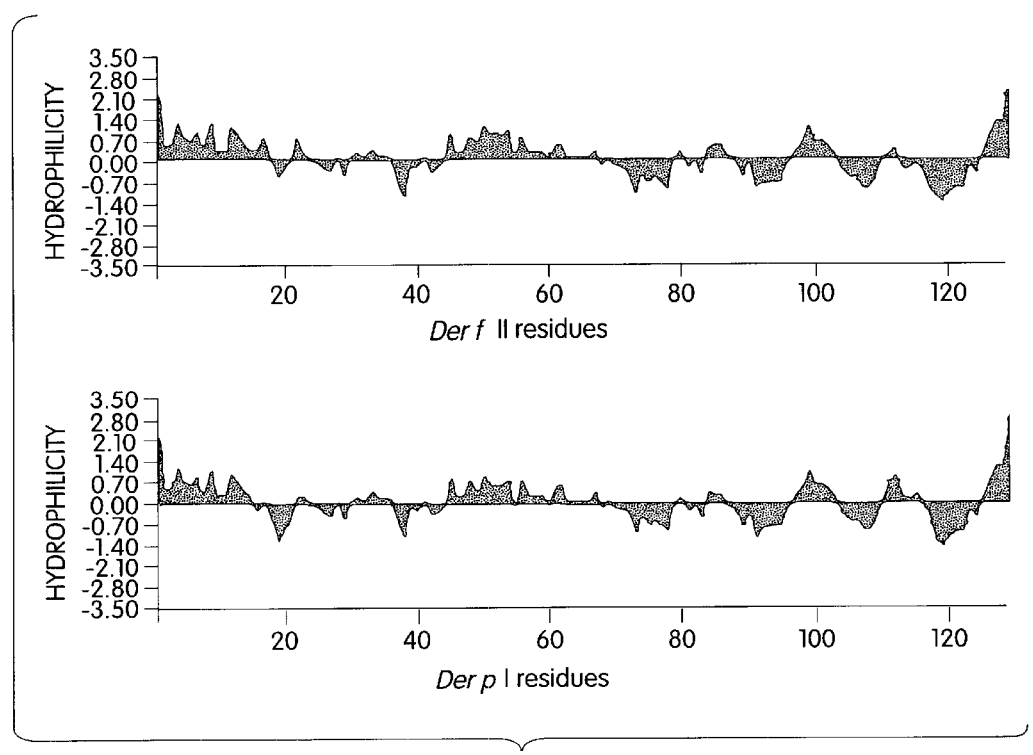

FIG. 10 is a hydrophilicity plot of *Der f* II and *Der p* II using the Hopp-Woods algorithm computed with the Mac Vector Sequence Analysis Software (IBI, New Haven) using a 6-residue window.

DETAILED DESCRIPTION OF THE INVENTION

The present invention relates to a nucleotide sequence coding for an allergen from the house dust mite Dermatophagoides and to the encoded Dermatophagoides protein or peptide which includes at least one epitope of the Dermatophagoides allergen. It particularly relates to a nucleotide sequence capable of expression in an appropriate host of a major allergen of *D. farinae*, such as *Der f* I or *Der f* II, or of a peptide which includes at least one epitope of *Der f* I or of *Der f* II. It also particularly relates to a nucleotide sequence capable of expression in an appropriate host of a major allergen of *D. pteronyssinus*, such as *Der p* I or *Der p* II, or of a peptide which includes at least one epitope of *Der p* I or of *Der p* II. The Dermatophagoides nucleotide sequence is useful as a probe for identifying additional nucleotide sequences which hybridize to it and encode other mite allergens, particularly *D. farinae* or *D. pteronyssinus* allergens. Further, the present invention relates to nucleotide sequences which hybridize to a *D. farinae* protein-encoding nucleotide sequence or a *D. pteronyssinus* protein-encoding nucleotide sequence but which encode a protein from another species or type of house dust mite, such as *D. microceras* (e.g., *Der m* I and *Der m* II).

The encoded Dermatophagoides mite allergen or peptide which includes at least one Dermatophagoides (*Der f* I or *Der f* II; *Der p* I or *Der p* II) epitope can be used for diagnostic purposes (e.g., as an antigen) and for therapeutic purposes (e.g., to desensitize an individual). Alternatively, the encoded house dust mite allergen can be a protein or peptide, such as a *D. microceras* protein or peptide, which displays the antigenicity of or is cross-reactive with a *Der f* or a *Der p* allergen; generally, these have a high degree of amino acid homology.

Accordingly, the present invention also relates to compositions which include a Dermatophagoides allergen (e.g., *Der f* I or allergen, *Der f* II allergen; *Der p* I or *Der p* II allergen or other D. allergen cross-reactive therewith) or a peptide which includes at least one epitope of a Dermatophagoides allergen (*Der f* I, *Der f* II, *Der p* I, *Der p* II or other D. allergen cross-reactive therewith) individually or in combination, and which can be used for therapeutic applications (e.g., desensitization). As is described below, DNA coding for major allergens from house dust mites have been isolated and sequenced. In particular, and as is described in greater detail in the Examples, two cDNA clones, coding, respectively, for *Der f* I allergen and *Der f* II allergen, have been isolated and sequenced. The nucleotide sequences of *Der p* I and *Der p* II have also been determined. The nucleotide sequence of each of these clones has been compared with that of the homologous allergen from the related mite *D. pteronyssinus* (*Der p* I and *Der p* II, respectively), as has the predicted amino acid sequence of each.

The following is a description of isolation and sequencing of the two cDNA clones coding for *Der f* allergens and their comparison with the corresponding *D. pteonyssinus* allergen and a description of use of the nucleotide sequences and encoded products in a diagnostic or a therapeutic context.

Isolation and Sequence Analysis of *Der f* I

Figure 1:
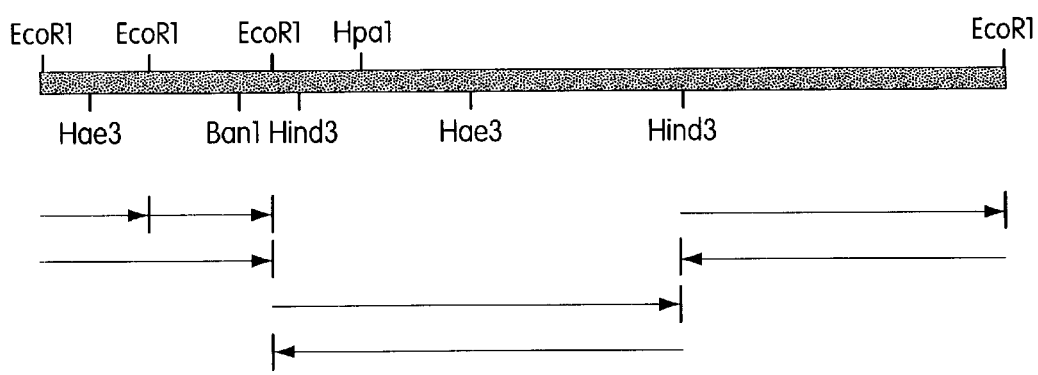
FIG. 1 is a restriction map of the cDNA insert of clone λgt11 f 1, including a schematic representation of the strategy of DNA sequencing. Arrows indicate directions in which sequences were read.

A cDNA clone coding for *Der f* I, a major allergen from the house dust mite *D. farinae*, has been isolated and sequenced. A restriction map of the cDNA insert of the clone is represented in FIG. 1, as is the strategy of DNA sequencing. This *Der f* I cDNA clone contains a 1.1-kb cDNA insert encoding a typical signal peptide, a proenzyme region and the mature *Der f* I protein. The product is 321 amino acid residues: a putative 18 residue signal peptide, an 80 residue proenzyme (pro-peptide) region, and a 223 residue mature enzyme region. The derived molecular weight is 25,191. The nucleotide sequence and the predicted amino acid sequence of the *Der f* I cDNA are represented in FIG. 2. The deduced amino acid sequence shows significant homology to other cysteine proteases in the pro-region, as well as in the mature protein. Sequence alignment of the mature *Der f* I protein with the homologous allergen *Der p* I from the related mite *D. pteronyssinus* (FIG. 3) revealed a high degree of homology (81%) between the two proteins, as predicted by previous sequencing at the protein level. In particular, the residues comprising the active site of these enzymes were conserved and a potential N-glycosylation site was present at equivalent positions in both mite allergens.

Conserved cysteine residue pairs (31, 71) and (65, 103), where the numbering refers to *Der p* I, are apparently involved in disulphide bond formation on the basis of the assumed similarity of the three dimensional structure of *Der p* I and *Der f* I to that of papain and actinidin, which also have an additional disulphide bridge. The fifth and final cysteine residue for which there is a homologous cysteine residue in papain and actinidin is the active site cysteine (residue 35 in *Der f* I). It is not unlikely that the two extra cysteine residues present in *Der p* I and *Der f* I may be involved in forming a third disulphide bridge.

The potential N-glycosylation site in *Der p* I is also present at the equivalent position in *Der f* I, with conservation of the crucial first and last residues of the tripeptide site. The degree of glycosylation of *Der f* I and *Der p* I has yet to be determined. Carbohydrates, including mannose, galactose, N-acetylglucosamine and N-acetylgalactosamine, have been reported in purified preparations of these mite allergens (Chapman, M. D., *J. Immunol.*, 125:587–592 (1980); Wolden, S. et al., *Int. Arch. Allergy Appl. Immunol.*, 68:144–151 (1982)).

Given the degree of homology over the first thirty N-terminal amino acid residues between mature *Der p* I and *Der m* I (70%) and mature *Der f* I and *Der m* I (97%) with the *Der m* I residues determined by conventional amino acid sequencing (Platts-Mills TAE et al., In: *Mite Allergy, a World-Wide Problem*, 27–29 (1988); Lind, P. and N. Horn, In: *Mite Allergy, a World-Wide Problem*, 30–34 (1988)), it is probable that the full mature *Der m* I sequence will confirm an overall 70–80% homology between the Group I mite allergens. *Der m* I is an allergen from *D. microceras*. High homology between the proenzyme moieties of *Der p* I and *Der f* I (91%) over the residues −23 to −1 and the structural analysis of *Der f* I suggests that the Group I allergens are likely to have N-terminal extension peptides of the mature protein of homologous structure and, at least for the pro-peptide, composition.

Studies on the fine structure of the design of signal sequences have identified three structurally dissimilar regions so far: a positively charged N-terminal (n) region, a central hydrophobic (h) region and a more polar C-terminal (c) region that seems to define the cleavage site (Von Heijne, G., *EMBO J.*, 3:2315–2323 (1984); *Eur. J. Biochem.*, 133:17–21 (1983); *J. Mol. Biol.*, 184:99–105 (1985)). Analysis of the signal peptide of *Der f* I revealed that it, too, contained these regions (FIG. 4). The n-region is extremely variable in length and composition, but its net charge does not vary appreciably with the overall length, and has a mean value of about +1.7. The n-region of the *Der f* I signal peptide, with a length of two residues, has a net charge of +2 contributed by the initiator methionine (which is unformylated and hence positively charged in eukaryotes) and the adjacent lysine (Lys) residue. The h-region of *Der f* I is enriched with hydrophobic residues, the characteristic feature of this region, with only one hydrophilic residue serine (Ser) present which can be tolerated. The overall amino acid composition of the *Der f* I c-region is more polar than that of the h-region as is found in signal sequences with the h/c boundary located between residues −6 and −5, which is its mean position in eukaryotes. Thus, the *Der f* I pre-peptide sequence appears to fulfill the requirements to which a functional signal sequence must conform.

While the signal sequence of *Der f* I and other cysteine proteases share structural homology, all being composed of the n, h and c-regions, they are highly variable with respect to overall length and amino acid sequence, as is clear in FIG. 4. However, significant sequence homology has been shown between the pro-regions of cysteine protease precursors (Ishidoh, K. et al., *FEBS Letters*, 226:33–37 (1987)). Alignment of the proenzyme regions of *Der f* I and a number of other cysteine proteases (FIG. 4) indicated that these pro-regions share a number of very conserved residues as well as semi-conserved residues which were present in over half of the sequences. This homology was increased if conservative amino acids such as valine (Val), isoleucine (Ile) and leucine (Leu) (small hydrophobic residues) or arginine (Arg) and Lys (positively charged residues) were regarded as identical. The *Der f* I proregion possessed six out of the seven highly conserved amino acids and all the residues at sites of conservative changes. The homology at less conserved sites was lower. Homology in the pro-peptide, in particular the highly conserved residues, may be important when considering the function of the pro-peptide in the processing of these enzymes, since it indicates that these sequences probably have structural and functional similarities.

Highly cross-reactive B cell epitopes on *Der f* I and *Der p* I have been demonstrated using antibodies present in mouse, rabbit and human sera (Heymann, P. W. et al., *J. Immunol*, 137:2841–2847 (1986); Platts-Mills, TAE et al., *J. Allergy Clin. Immunol.*, 78:398–407 (1986)). However, species-specific epitopes have also been defined in these systems. Murine monoclonal antibodies bound predominantly to species-specific determinants (Platts-Mills TAE et al., *J. Immunol*,. 139:1479–1484 (1987). Some 40% of rabbit anti-*Der p* I reactivity was accounted for by epitopes unique to *Der p* I (Platts-Mills, TAE et al., *J. Allergy Clin. Immunol.*, 78:398–407 (1986)), and some species-specific binding of antibodies from allergic humans was observed, although the majority bind to cross-reactive epitopes (Platts-Mills TAE et al., *J. Immunol.*, 139:1479–1484 (1987).

The recombinant DNA strategy of gene fragmentation and expression was used (Greene, W. K. et al., *Immunol.* (1990)) to define five antigenic regions of recombinant *Der p* I which contained B cell epitopes recognized by a rabbit anti-*Der p* I antiserum. Using the technique of immunoabsorption, three of these putative epitopes were shown to be shared with *Der f* I (located on regions containing amino acid residues 34–47, 60–72 and 166–194) while two appeared to be specific for *Der p* I (regions 82–99 and 112–140). Differences in the reactivity of these peptides to rabbit anti-*D. farinae* supported the above division into cross-reactive and species-specific epitopes. The sequence differences shown between the *Der p* I and the *Der f* I proteins are primarily located in the N and C terminal regions, as well as in an extended surface loop (residues 85–136) linking the two domains of the enzyme that includes helix D (residues 127–136), as predicted from the secondary and tertiary structures of papain and actinidin (Baker, E. N. and J. Drenth, In: *Biological Macromolecules and Assemblies*, Vol. 3, pp. 314–368, John Wiley and Sons, NY. (1987)). The surface location of these residues is supported by the hydrophilicity plots of *Der p* I and *Der f* I in FIG. 5, which illustrate the predominantly hydrophilic nature of this region that predicts surface exposure. This region also contains the two species-specific B cell epitopes recognized by the rabbit anti-*Der p* I serum (see above). Analysis of the sequences in the regions containing the cross-reactive epitopes showed that two of the cross-reactive epitopes (located in regions 34–47 and 60–72) are completely conserved between *Der p* I and *Der f* I, while the majority of residues in a third cross-reactive epitope-containing region (residues region 166–194) were conserved.

Expression of results in production of pre-pro-*Der f* I protein in *E. coli* a recombinant protein of greater solubility, stability and antigenicity than that of recombinant *Der p* I. Protein encoded by *Der f* I cDNA has been expressed using a pGEX vector and has been shown by radioimmune assay to react with rabbit anti-*D. farinae* antibodies. The availability of high yields of soluble *Der f* I allergen and antigenic derivatives will facilitate the development of diagnostic and therapeutic agents and the mapping of B and T cell antigenic determinants.

With the availability of the complete amino acid sequence of recombinant *Der f* I, mapping of the epitopes recognized by both the B and T cell compartments of the immune system can be carried out. The use of techniques such as the screening of overlapping synthetic peptides, the use of monoclonal antibodies and gene fragmentation and expression should enable the identification of both the continuous and topographical epitopes of *Der f* I. It will be particularly useful to determine whether allergenic (IgE-binding) determinants have common features and are intrinsically different from antigenic (IgG-binding) determinants and whether T cells recognize unique epitopes different from those recognized by B cells. Studies to identify the *Der f* I epitopes reactive with mite allergic human IgE antibodies and the division of these into determinants cross-reactive with *Der p* I and determinants unique to *Der f* I can also be carried out. B cell (and T cell) epitopes specific for either species can be used to provide useful diagnostic reagents for determining reactivity to the different mite species, while cross-reacting epitopes are candidates for a common immuno-therapeutic agent.

As described in co-pending Application U.S. Ser. No. 458,643, incorporated herein by reference, the molecular cloning of mite allergens resulted in the isolation of a cDNA clone coding for *Der p* I which contained a 0.8-kb cDNA insert. Sequence analysis revealed that the 222 amino acid residue mature recombinant *Der p* I protein showed significant homology with a group of cysteine proteases, including actinidin, papain, cathepsin H and cathepsin B.

Isolation and Sequence Analysis of *Der f* II

A cDNA clone coding for *Der f* II, a major allergen from the house dust mite *D. farinae*, has been isolated and sequenced, as described in Example 2. The nucleotide sequence and the predicted amino acid sequence of the *Der f* II cDNA are represented in FIG. 6. A restriction map of the cDNA insert of a clone coding for *Der f* II is represented in FIG. 8.

FIG. 9 shows the alignment of *Der f* II and *Der p* II cDNA sequences.

The homology of the sequence of *Der f* II with Derby II (88%) is higher than the 81% homology found with *Der p* I and *Der f* I, which is significantly different (p<0.05) using the chi$^2$ distribution. The reason for this may simply be that the Group I allergens are larger and each residue may be less critical for the structure and function of the molecule. It is known; for example, that assuming they adopt a similar conformation to other cysteine proteases, many of the amino acid differences in *Der p* I and *Der f* I lie in residues linking the two domain structures of the molecules. The 6 cysteine molecules are conserved between the group II allergens, suggesting a similar disulphide bonding, although this may be expected, given the high overall homology. Another indication of the conservation of these proteins is that 34/55 of the nucleotide changes of the coding sequence are in the third base of a codon, which usually does not change the amino acid. Residues that may be of importance in the function of the molecule are Ser 57 where all three bases are changed but the amino acid is conserved. A similar phenomenon exists at residue 88, where a complete codon change has conserved a small aliphatic residue. Again, like *Der p* II, the *Der f* II cDNA clone does not have a poly A tail, although the 3' non-coding region is rich in adenosine and has two possible polyadenylation signals ATAA. The nucleotides encoding the first four residues are from the PCR primer which was designed from the known homology of *Der p* II and *Der f* II from N-terminal amino acid sequencing. A primer based on the C-terminal sequence can now be used to determine these bases, as well as the signal sequence.

Uses of the Subject Allergenic Proteins/Peptides and DNA Encoding Same

The materials resulting from the work described herein, as well as compositions containing these materials, can be used in methods of diagnosing, treating and preventing allergic responses to mite allergens, particularly to mites of the genus Dermatophagoides, such as *D. farinae* and other species (e.g., *D. pteronyssinus* and *D. microceras*). In addition, the cDNA (or the mRNA from which it was transcribed) can be used to identify other similar sequences. This can be carried out, for example, under conditions of low stringency and those sequences having sufficient homology (generally greater than 40%) can be selected for further assessment using the method described herein. Alternatively, high stringency conditions can be used. In this manner, DNA of the present invention can be used to identify sequences coding for mite allergens having amino acid sequences similar to that of *Der f* I, *Der f* II, *Der p* I or *Der p* II. Thus, the present invention includes not only *Der f* and *Der p* II, but other mite allergens as well (e.g., other mite allergens encoded by DNA which hybridizes to DNA of the present invention).

Proteins or peptides encoded by the cDNA of the present invention can be used, for example, as "purified" allergens. Such purified allergens are useful in the standardization of allergen extracts or preparations which can be used as reagents for the diagnosis and treatment of allergy to house dust mites. Through use of the peptides of the present invention, allergen preparations of consistent, well-defined composition and biological activity can be made and administered for therapeutic purposes (e.g., to modify the allergic response of a house dust mite-sensitive individual). *Der f* I or *Der f* II peptides or proteins (or modified versions thereof, such as are described below) may, for example, modify B-cell response to *Der f* I or *Der f* II, T-cell response to *Der f* I and *Der f* II, or both responses. Similarly, *Der p* I or *Der p* II proteins or peptides may be used to modify B-cell and/or T-cell response to *Der p* I or *Der p* II. Purified allergens can also be used to study the mechanism of immunotherapy of allergy to house dust mites, particularly to *Der f* I, *Der f* II, *Der p* I and *Der p* II, and to design modified derivatives or analogues which are more useful in immunotherapy than are the unmodified ("naturally-occurring") peptides.

In those instances in which there are epitopes which are cross-reactive, such as the three epitopes described herein which are shared by *Der f* I and *Der p* I, the area(s) of the molecule which contain the cross-reactive epitopes can be used as common immunotherapeutic peptides to be administered in treating allergy to the two (or more) mite species which share the epitope. For example, the cross-reactive epitopes could be used to induce IgG blocking antibody against both allergens (e.g., *Der f* I and *Der p* I allergen). A peptide containing a univalent antibody epitope can be used, rather than the entire molecule, and may prove advantagious because the univalent antibody epitope cannot crosslink mast cells and cause adverse reactions during desensitizing treatments. It is also possible to attach a B cell epitope to a carrier molecule to direct T cell control of allergic responses.

Alternatively, it nay be desirable or necessary to have peptides which are specific to a selected Dermatophagoides allergen. As described herein, two epitopes which are apparently *Der p* I-specific have been identified. A similar approach can be used to identify other species-specific epitopes (e.g., *Der p* I or II, *Der f* I or II. The presence in an individual of antibodies to the species-specific epitopes can be used as a quick serological test to determine which mite species is causing the allergic response. This would make it possible to specifically target therapy provided to an individual to the causative species and, thus, enhance the therapeutic effect.

Work by others has shown that high doses of allergens generally produce the best results (i.e., best symptom relief). However, many people are unable to tolerate large doses of allergens because of allergic reactions to the allergens. Modification of naturally-occurring allergens can be designed in such a manner that modified peptides or modified allergens which have the same or enhanced therapeutic properties as the corresponding naturally-occurring allergen but have reduced side effects (especially, anaphylactic reactions) can be produced. These can be, for example, a peptide of the present invention (e.g., one having all or a portion of the amino acid sequence of Der f I or Der f II, Der p I or Der p II). Alternatively, a combination of peptides can be administered. A modified peptide or peptide analogue (e.g., a peptide in which the amino acid sequence has been altered to modify immunogenicity and/or reduce allergenicity or to which a component has been added for the same purpose) can be used for desensitization therapy.

Administration of the peptides of the present invention to an individual to be desensitized can be carried out using known techniques. A peptide or combination of different peptides can be administered to an individual in a composition which includes, for example, an appropriate buffer, a carrier and/or an adjuvant. Such compositions will generally be administered by injection, inhalation, transdermal application or rectal administration. Using the information now available, it is possible to design a Der f I or Der f II peptide which, when administered to a sensitive individual in sufficient quantities, will modify the individual's allergic response to a Der f I and/or Der f II. This can be done, for example, by examining the structures of Der f I or Der f II, producing peptides to be examined for their ability to influence B-cell and/or T-cell responses in house dust mite-sensitive individuals and selecting appropriate epitopes recognized by the cells. Synthetic amino acid sequences which mimic those of the epitopes and which are capable of down regulating allergic response to Der f I or Der f II allergen can be made. Proteins, peptides or antibodies of the present invention can also be used, in known methods, for detecting and diagnosing allergic response to Der f I or Der f II. For example, this can be done by combining blood obtained from an individual to be assessed for sensitivity to one of these allergens with an isolated allergenic peptide of house dust mite, under conditions appropriate for binding of or stimulating components (e.g., antibodies, T cells, B cells) in the blood with the peptide and determining the extent to which such binding occurs. The Der p I and Der p II proteins or peptides can be used in a similar manner for desensitization and diagnosis of sensitivity. Der f and Der p proteins or peptides can be administered together to treat an individual sensitive to both allergen types.

It is now also possible to design an agent or a drug capable of blocking or inhibiting the ability of Der f I or Der f II to induce an allergic reaction in house dust mite-sensitive individuals. Such agents could be designed, for example, in such a manner that they would bind to relevant anti-Der f I or anti-Der f II IgEs, thus preventing IgE-allergen binding and subsequent mast cell degranulation. Alternatively, such agents could bind to cellular components of the immune system, resulting in suppression or desensitization of the allergic response to these allergens. A non-restrictive example of this is the use of appropriate B- and T-cell epitope peptides, or modifications thereof, based on the cDNA/protein structures of the present invention to suppress the allergic response to Der f I or Der f II allergens. This can be carried out by defining the structures of B- and T-cell epitope peptides which affect B- and T-cell function in in vitro studies with blood cells from Der f I or Der f II-sensitive individuals. This can also be applied to Der p I or Der p II, in order to block allergic response to these allergens.

The cDNA encoding Der f I or Der f II or peptide including at least one epitope can be used to produce additional peptides, using known techniques such as gene cloning. A method of producing a protein or a peptide of the present invention can include, for example, culturing a host cell containing an expression vector which, in turn, contains DNA encoding all or a portion of a selected allergenic protein or peptide (e.g., Der f I, Der f II or a peptide including at least one epitope). Cells are cultured under conditions appropriate for expression of the DNA insert (production of the encoded protein or peptide). The expressed product is then recovered, using known techniques. Alternatively, the allergen or portion thereof can be synthesized using known mechanical or chemical techniques. As used herein, the term protein or peptide refers to proteins of peptides made by any of these techniques. The resulting peptide can, in turn, be used as described previously.

DNA to be used in any embodiment of this invention can be cDNA obtained as described herein or, alternatively, can be any oligodeoxynucleotide sequence having all or a portion of the sequence represented in FIGS. 2 and 6, or their functional equivalent. Such oligodeoxynucleotide sequences can be produced chemically or mechanically, using known techniques. A functional equivalent of an oligonucleotide sequence is one which is capable of hybridizing to a complementary oligonucleotide sequence to which the sequence (or corresponding sequence portions) of FIGS. 2 and 6 hybridizes and/or which encodes a product (e.g., a polypeptide or peptide) having the same functional characteristics of the product encoded by the sequence (or corresponding sequence portion) represented in these figures. Whether a functional equivalent must meet one or both criteria will depend on its use (e.g., if it is to be used only as an oligoprobe, it need meet only the first criterion and if it is to be used to produce house dust mite allergen, it need only meet the second criterion).

The structural information now available (e.g., DNA, protein/peptide sequences) can also be used to identify or define T cell epitope peptides and/or B cell epitope peptides which are of importance in allergic reactions to D. farinae allergens and to elucidate the mediators or mechanisms (e.g., interleukin-2, interleukin-4, gamma interferon) by which these reactions occur. This knowledge should make it possible to design peptide-based house dust mite therapeutic agents or drugs which can be used to modulate these responses.

The present invention will now be further illustrated by the following Examples, which are not intended to be limiting in any way.

EXAMPLES

Example 1

Isolation and Characterization of cDNA Coding for Der f I

MATERIALS AND METHODS

*Dermatophagoides farinae* culture

Mites were purchased from Commonwealth Serum Laboratories, Parkville, Australia.

Construction of the *D. farinae* cDNA λgt11 Library

Polyadenylated mRNA was isolated from live *D. farinae* mites and cDNA was synthesized by the RNase H method (Gubler, V. and B. J. Hoffman, *Gene*, 25:263–269 (1983))

using a kit (Amersham International, Bucks.). After the addition of EcoRI linkers (New England Biolabs, Beverly, Mass.) the cDNA was ligated to alkaline phosphatase treated λgt11 arms (Promega, Madison, Wis.). The ligated DNA was packaged and plated in *E. coli* Y1090 (r-) to produce a library of $2 \times 10^4$ recombinants.

Isolation of *Der f* I cDNA Clones from the *D. farinae* cDNA λgt11 Library

Screening of the library was performed by hybridization with two probes comprising the two *Der p* I cDNA BamHI fragments 1–348 and 349–857 generated by BamHI digestion of a derivative of the *Der p* I cDNA which has had two-BamHI restriction sites inserted between amino acid residues −1 and 1 and between residues 116 and 117 by site-directed mutagenesis (Chua, K. Y. et al., *J. Exp. Med.*, 167:175–182 (1988)). The probes were radiolabelled with $^{32}P$ by nick translation. Phage were plated at 20,000 pfu per 150 mm petri dish and plaques were lifted onto nitrocellulose (Schleicher and Schull, Dassel, F R G), denatured and baked (Maniatis, T. et al., *Molecular cloning: A Laboratory Manual*, Cold Spring Harbor Laboratory Press (1982)). Prehybridizations were performed for 2 hours at 42° C. in 50% formamide/5×SSCE/1×Denhardt's/poly C (0.1 mg/ml)/poly U(0.1 mg/ml) with hybridization overnight at 42° C. at $10^6$ cpm/ml. Post hybridization washes consisted of 15 min washes at room temperature with 2×sodium chloride citrate (SSC)/0.1% sodium dodecylsulphate (SDS), 0.5×SSC/0.1% SDS, 0.1×SSC/0.1% SDS successively and a final wash at 50° C. for 30 min in 0.1×SSC/1% SDS.

Isolation of DNA from λyt11 f 1 cDNA Clones

Phage DNA from λgt11 f 1 clones was prepared by a rapid isolation procedure. Clarified phage plate lysate (1 ml) was mixed with 270 μL of 25% wt/vol polyethylene glycol (PEG 6000) in 2.5 M NaCl and incubated at room temperature for 15 min. The mixture was then spun for 5 min in a microfuge (Eppendorf, F R G), and the supernatant was removed. The pellet was dissolved in 100 μL of 10 mM Tris/HCl pH8.0 containing 1 mM EDTA and 100 mM NaCl (TE). This DNA preparation was extracted with phenol/TE, the phenol phase was washed with 100 μl TE, the pooled aqueous phases were then extracted another 2 times with phenol/TE, 2 times with Leder phenol (phenol/chloroform/isoamylalcohol; 25:24:1), once with chloroform and the DNA was precipitated by ethanol.

DNA Sequencing

To obtain clones for DNA sequence analysis, the λgt11 f1 phage DNA was digested with EcoRI restriction enzyme (Pharmacia, Uppsala, Sweden) and the DNA insert was ligated to EcoRI-digested M13-derived sequencing vectors mp18 and mp19 (Maniatis, T. et al., *Molecular Cloning: A Laboratory Manual*, Cold Spring Harbor Laboratory Press (1982)). Transformation was carried out using *E. coli* TG-1 and sequencing was performed by the dideoxynucleotide chain termination method (Sanger, F. et al., *Proc. Natl. Acad. Sci. USA*, 74:5463–5467 (1977)) using the Sequenase version 2.0 DNA sequencing kit (U. S. B., Cleveland, Ohio).

Polymerase Chain Reaction(PCR)

PCR was performed by the Taq DNA polymerase method (Saiki, R. K. et al., *Science*, 239:487–491 (1988)) using the TaqPaq kit (Biotech International, Bentley, Wash.) and the conditions recommended by the supplier with long of target DNA and 10 pmol of λgt11 primers (New England BioLabs, Beverly, Mass.).

RESULTS

Isolation of *Der f* I cDNA clones

Two clones expressing the major mite allergen *Der f* I were isolated from the *D. farinae* cDNA λgt11 library by their ability to hybridize with both of the *Der p* I cDNA probes (nucleotides 1–348 and 349–857). This approach was adopted because amino acid sequencing had shown high homology (80%) between these two allergens (Thomas, W. R. et al., *Advances in the Biosciences*, 14:139–147 (1989)). Digestion of the λgt11 f1 clone DNA with EcoRI restriction enzyme to release the cDNA insert produced three *Der f* I cDNA EcoRI fragments: one approximately 800 bases long and a doublet approximately 150 bases long. The *Der f* I cDNA insert was also amplified from the phage DNA by the polymerase chain reaction (PCR) resulting in a PCR product of approximately 1.1-kb. Each *Der f* I cDNA fragment was cloned separately into the M13-derived sequencing vectors mp18 and mp19 and sequenced.

DNA Sequence Analysis

The nucleotide sequence of the *Der f* I cDNA was determined using the sequencing strategy shown in FIG. 1. The complete sequence was shown to be 1084 bases long and included a 335-base long 5' proximal end sequence, a coding region for the entire native *Der f* I protein of 223 amino acids with a derived molecular weight of 25,191 and an 80-base long 3' noncoding region (FIG. 2). The assignment of the threonine residue at position 1 as the $NH_2$-terminal amino acid of *Der f* I was based on data obtained by $NH_2$-terminal amino acid sequencing of the native protein and the predicted amino acid sequence of recombinant *Der p* I (Chua, K. Y. et al., *J. Exp. Med.*, 167:175–182 (1988)). The predicted amino acid sequence of the *Der f* I cDNA in the $NH_2$-terminal region matched completely with that determined at the protein level (FIG. 2).

The complete mature protein is coded by a single open reading frame terminating at the TGA stop codon at nucleotide position 1007–1009. The first ATG codon at nucleotide position 42–44 is presumed to be the translation initiation site since the subsequent sequence codes for a typical signal peptide sequence.

Amino Acid Sequence Analysis

The amino acid sequence predicted by nucleotide analysis is shown in FIG. 2. As shown in the composite alignment of the amino acid sequence of mature *Der p* I and *Der f* I (FIG. 3), high homology was observed between the two proteins. Sequence homology analysis revealed that the *Der f* I protein showed 81% homology with the *Der p* I protein as predicted by previous conventional amino acid sequencing. In particular, the residues making up the active site of *Der p* I, based on those determined for papain, actinidin, cathepsin H. and cathepsin B, are also conserved in the *Der f* I protein. The residues are glutamine (residue 29), glycine, serine and cysteine (residues 33–35), histidine (residue 171) and asparagine, serine and tryptophan (residues 191–193) where the numbering refers to *Der f* I. The predicted mature *Der f* I amino acid sequence contains a potential N-glycosylation site (Asn-Thr-Ser) at position 53–55 which is also present as Asn-Gln-Ser at the equivalent position in *Der p* I.

Analysis of the predicted amino acid sequence of the entire *Der f* I cDNA insert has shown that, as for other cysteine proteases (FIG. 4), the *Der f* I protein has pre- and proform intermediates. As previously mentioned, the methionine residue at position −98 is presumed to be the initiation methionine. This assumption is based on the fact that firstly, the 5' proximal end sequence from residues −98 to −81 is composed predominantly of hydrophobic amino acid residues (72%), which is the characteristic feature of signal peptides (Von Heijne, G., *EMBO J.*, 3:2315–2323 (1984)). Secondly, the lengths of the presumptive pre- (18 amino acid residues) and pro-peptides (80 residues) are similar to those for other cysteine proteases (FIG. 4). Most cysteine proteases examined have about 120 preproenzyme residues (of which an average of 19 residues form the signal peptide) with cathepsin B the smallest with 80 (Ishidoh, K. et al., *FEBS Letters*, 226:32–37 (1987)). *Der f* I falls within this range with a total of 98 preproenzyme residues.

By following the method for predicting signal-sequence cleavage sites outlined in Von Beijne, it is proposed that cleavage from the pre-*Der f* I sequence for proenzyme formation occurs at the signal peptidase cleavage site lying between Ala (−81) and Arg (−80) (Von Heijne, G., *Eur. J. Biochem.*, 133:17–21 (1988) and *J. Mol. Biol.*, 184:99–105 (1985)). Thus, the sequence from residues −98 to −81 codes for the leader peptide while the proenzyme moiety of *Der f* I begins at residue Arg (−80) and ends at residue Glu (−1).

Example 2
Isolation and Characterization of cDNA Coding for *Der f* II

MATERIALS AND METHODS
Amino acid sequence analysis
Preparation of λgt11 *D. farinae* cDNA Ligations

*D. farinae* was purchased from Commonwealth Serum Laboratories, Parkville, Australia, and used to prepare mRNA (polyadenylated RNA) as described (Stewart, G. A. and W. R. Thomas, *Int. Arch. Allergy Appl Immunol.*, 83:384–389 (1987)). The mRNA was suspended at approximately 0.5 µg/µl and 5 µg used to prepare cDNA by the RNase H method (Gubler, U. and Hoffman, B. J., *Gene*, 25:263–269 (1983)) using a kit (Amersham International, Bucks). EcoRI linkers (Amersham, GGAATTCC) were attached according to the method described by Huynh et al., Constructing and screening cDNA libraries in gt10 and gt11, In: Glover, DNA Cloning vol. A practical approach pp. 47–78 IRL Press, Oxford (1985)). The DNA was then digested with EcoRI and recovered from an agarose gel purification by electrophoresis into a DEAE membrane (Schleicher and Schuell, Dassel, FRG, NA-45) according to protocol 6.24 of Sambrook et al., (Sambrook et al., Molecular Cloning, A Laboratory Manual, 2d Ed, Cold Spring Harbor Laboratory Press (1989)), except 0.5M arginine base was used for elution. The cDNA was then ligated in λgt10 and λgt11 at an arms to insert ratio of 2:1. Some was packaged for plaque libraries and an aliquot retained for isolating sequences by polymerase chain reaction as described below.

Isolation of *Der f* II cDNA Polymerase Chain Reaction

To isolate *Der f* II cDNA, an oligonucleotide primer based on the N-terminal sequence of *Der p* II was made because their amino acid residues are identical in these regions (Heymann, P. W. et al., *J. Allergy Clin. Immunol.*, 83:1055–1087 (1989)). The primer GGATCCGATCAACTCGATGC-3' was used. The first GGATCC encodes a BamH1 site and the following sequence GAT... encodes the first 4 residues of *Der p* II. For the other primer the λgt11 TTGACACCAGACCAACTGGTAATG-3' reverse primer flanking the EcoRI cloning site was used (New England Biolabs, Beverly, Mass.). The *Der p* II primer was designed to have approximately 50–60% G-C and to end on the first or second, rather than the third, base of a codon (Gould, S. J. et al., *Proc. Natl. Acad. Sci.*, 86:1934–1938 (1989); Summer, R. and D. Tautz, *Nucleic Acid Res.*, 17:6749 (1989)).

The PCR reactions were carried out in a final reaction volume of 25 µl containing 67 mM Tris-HCL (pH8.8 at 25° C.), 16.6 mM $(NH_4)_2SO_4$, 40 µM dNTPs, 5 mM 2-mercaptoethanol, 6 µM EDTA, 0.2 mg/ml gelatin, 2 mM $MgCl_2$, 10 pmoles of each primer and 2 units of Taq polymerase. Approximately 0.001 µg of target DNA was added and the contents of the tube were mixed and overlayed with paraffin oil. The tubes were initially denatured at 95° C. for 6 minutes, then annealed at 55° C. for 1 minute and extended at 72° C. for 2 minutes. Thereafter for 38 cycles, denaturing was carried out for 30 seconds and annealing and extension as before. In the final (40th) cycle, the extension reaction was increased to 10 minutes to ensure that all amplified products were full length. The annealing temperature was deliberately set slightly lower than the Tm of the oligonucleotide primers (determined by the formula Tm=69.3+0.41(G+C %)−650/oligo length) to allow for mismatches in the N-terminal primer.

5 µl of the reaction was then checked for amplified bands on a 1% agarose gel. The remainder of the reaction mixture was extracted with chloroform to remove all of the paraffin oil and ethanol precipitated prior to purification of the amplified product on a low melting point agarose gel (Bio-Rad, Richmond, Calif.).

Subcloning of PCR Product

The ends of the purified PCR product were filled in a reaction containing 10 mM Tris HCl, 10 mM $MgCl_2$, 50 mM NaCl, 0.025 mM dNTP and 1 µl of Klenow enzyme in a final volume of 100 µl. The reaction was carried out at 37° C. for 15 minutes and heat inactivated at 70° C. for 10 minutes. The mixture was Leder phenol extracted before ethanol precipitation. The resulting blunt ended DNA was ligated into M13mp18 digested with Sma I in a reaction containing 0.5M ATP, 1×ligase buffer and 1 unit of $T_4$ ligase at 15° C. for 24 hrs and transformed into *E. coli* TG1 made competent by the $CaCl_2$ method. The transformed cells were plated out as a lawn on L+G plates and grown overnight at 37° C.

Preparation of Single-stranded DNA Template for Sequencing

Isolated white plaques were picked using an orange stick into 2.5 ml of an overnight culture of TG1 cells diluted 1 in 100 in 2×TY broth, and grown at 37° C. for 6 hours. The cultures were pelleted and the supernatant removed to a fresh tube. To a 1 ml aliquot of this supernatant 270 µl of 20% polyethylene glycol, 2.5 M NaCl was added and the tube was vortexed before allowing it to stand at RT for 15 minutes. This was then spun down again and all traces of the supernatant were removed from the tube. The pellet was then resuspended in 100 µl of 1×TE buffer. At least 2 phenol:TE extractions were done, followed by 1 Leder phenol extraction and a $CHCL_3$ extraction. The DNA was precipitated in ethanol and resuspended in a final volume of 20 µl of TE buffer.

DNA Analysis

DNA sequencing was performed with the dideoxynucleotide chain termination (Sanger, F et al., *Proc. Nat. Acad. Sci.*, 74:5463–5467 (1977)) using DNA produced from M13 derived vectors mp18 and mp19 in *E. coli* TG1 and T4 DNA polymerase (Sequenase version 2.0, USB Corp., Cleveland, Ohio; Restriction endonucleases were from Toyobo, (Osaka, Japan). All general procedures were by standard techniques (Sambrook, J. et al., A Laboratory Manual, 2d Ed. Cold Spring Harbor Laboratory Press (1989)). The sequence analysis was performed using the Mac Vector Software (IBI, New Haven, Conn.).

RESULTS

*D. farinae* cDNA ligated in λgt11 was used to amplify a sequence using an oligonucleotide primer with homology to nucleotides coding for the 4 N terminal residues of *Der p* II and a reverse primer for the λgt11 sequence flanking the coding site. Two major bands of about 500 bp and 300 bp were obtained when the product was gel electrophoresed. These were ligated into M13 mp18 and a number of clones containing the 500 bp fragment were analyzed by DNA sequencing. Three clones produced sequence data from the N-terminal primer end and one from the other orientation. Where the sequence data from the two directions overlapped, a complete match was found. One of the clones read from the N-terminal primer, contained a one-base deletion which shifted the reading frome. It was deduced to be a copying error, as the translated sequence from the other two clones matched the protein sequence for the first 20 amino acid residues of the allergen.

The sequence of the clones showing consensus and producing a correct reading frame is shown in FIG. 6, along with the inferred amino acid sequence. It coded for a 129 residue protein with no N-glycosylation site and a calculated molecular weight of 14,021 kD. No homology was found when compared to other proteins on the GenBank data base (61.0 release). It did, however, show 88% amino acid residue homology with Der p II shown in the alignment in FIG. 9. Seven out of the 16 changes were conservative. The conserved residues also include all the cysteines present at positions 8, 21, 27, 73, 78 and 119. There was also considerable nucleotide homology, although the restriction enzyme map generated from the sequence data for commonly used enzymes is different from Der p II (FIG. 8). The hydrophobicity plots of the translated sequence of Der f II and Der p II shown in FIG. 10 are almost identical.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated DNA encoding a peptide from a protein allergen selected from the group consisting of a Der f I protein allergen comprising the amino acid sequence shown in FIG. 2 and a Der f II protein allergen comprising the amino acid sequence shown in FIG. 6, wherein the peptide comprises at least one epitope of said protein allergen, provided that said epitope does not cross-react with a Der p I protein allergen or a Der p II protein allergen.

2. The isolated DNA of claim 1 comprising a portion of the nucleotide sequence shown in FIG. 2.

3. The isolated DNA of claim 1 comprising a portion of the nucleotide sequence shown in FIG. 6.

4. The isolated DNA of claim 1 encoding a peptide comprising amino acid residues 34–47 of the amino acid sequence shown in FIG. 2.

5. The isolated DNA of claim 1 encoding a peptide comprising amino acid residues 60–72 of the amino acid sequence shown in FIG. 2.

6. The isolated DNA of claim 1 encoding a peptide comprising amino acid residues 166–194 of the amino acid sequence shown in FIG. 2.

7. An expression vector comprising the nucleic acid of claim 1.

8. The isolated DNA of claim 1, wherein the epitope is a T cell epitope or a B cell epitope.

9. A host cell transfected with the expression vector of claim 7.

10. The host cell of claim 9 which is a eukaryotic cell.

11. A method of producing a peptide from a protein allergen selected from the group consisting of a Der f I protein allergen and a Der f II protein allergen, comprising culturing the host cell of claim 10 in medium to express the peptide and isolating the peptide from the culture.

* * * * *